United States Patent
Glerum et al.

(10) Patent No.: US 11,883,076 B2
(45) Date of Patent: Jan. 30, 2024

(54) INTRADISCAL ANCHOR FIXATION DEVICE AND METHOD

(71) Applicant: GLOBUS MEDICAL, INC., Audubon, PA (US)

(72) Inventors: Chad Glerum, Pennsburg, PA (US); Mark Weiman, Downingtown, PA (US); Tyler Hessler, Phoenixville, PA (US); Albert Hill, Richboro, PA (US)

(73) Assignee: Globus Medical, Inc, Audubon, PA (US)

( * ) Notice: Subject to any disclaimer, the term of this patent is extended or adjusted under 35 U.S.C. 154(b) by 487 days.

(21) Appl. No.: 16/589,519

(22) Filed: Oct. 1, 2019

(65) Prior Publication Data
US 2021/0093360 A1    Apr. 1, 2021

(51) Int. Cl.
  *A61F 2/44* (2006.01)
  *A61B 17/70* (2006.01)
  *A61B 17/00* (2006.01)
  *A61F 2/30* (2006.01)

(52) U.S. Cl.
  CPC ........ *A61B 17/7034* (2013.01); *A61F 2/4455* (2013.01); *A61B 2017/00402* (2013.01); *A61F 2002/30579* (2013.01)

(58) Field of Classification Search
  CPC .. A61F 2002/30579; A61F 2002/30841; A61F 2/4455
  See application file for complete search history.

(56) References Cited

U.S. PATENT DOCUMENTS

| | | | |
|---|---|---|---|
| 8,267,997 B2* | 9/2012 | Colleran | A61F 2/4611 623/17.11 |
| 8,460,388 B2* | 6/2013 | Kirwan | A61F 2/4611 623/17.11 |
| 9,044,337 B2* | 6/2015 | Dinville | A61F 2/4455 |
| 9,161,842 B2* | 10/2015 | Chin | A61F 2/4455 |
| 9,775,722 B2* | 10/2017 | Kim | A61F 2/447 |
| 10,456,268 B2* | 10/2019 | Mercier | A61B 17/7064 |
| 10,561,502 B2* | 2/2020 | Bernard | A61F 2/447 |
| 10,765,531 B2* | 9/2020 | Kim | A61F 2/4611 |
| 10,765,532 B2* | 9/2020 | Ashleigh | A61F 2/4611 |
| 2006/0190080 A1* | 8/2006 | Danoff | A61F 2/30721 623/17.11 |
| 2011/0172774 A1* | 7/2011 | Varela | A61F 2/447 623/17.16 |
| 2011/0196494 A1* | 8/2011 | Yedlicka | A61F 2/4455 623/17.16 |
| 2014/0074241 A1* | 3/2014 | McConnell | A61F 2/447 623/17.16 |
| 2014/0379085 A1* | 12/2014 | Duffield | A61F 2/4455 623/17.16 |
| 2015/0320568 A1* | 11/2015 | Ameil | A61F 2/4637 623/17.13 |
| 2016/0338851 A1* | 11/2016 | Ashleigh | A61F 2/4455 |
| 2017/0311997 A1* | 11/2017 | Lequette | A61B 17/72 |
| 2020/0046514 A1* | 2/2020 | Gilbride | A61F 2/30749 |

FOREIGN PATENT DOCUMENTS

EP          3354234 A1 *  8/2018  ............. A61F 2/447

* cited by examiner

*Primary Examiner* — Lynnsy M Summitt

(57) ABSTRACT

Intradiscal fixation device assemblies, systems, and methods thereof. An intradiscal anchor fixation device includes an anchor block and at least one anchor attached to or extending through the anchor block to anchor the device to a vertebral body.

8 Claims, 9 Drawing Sheets

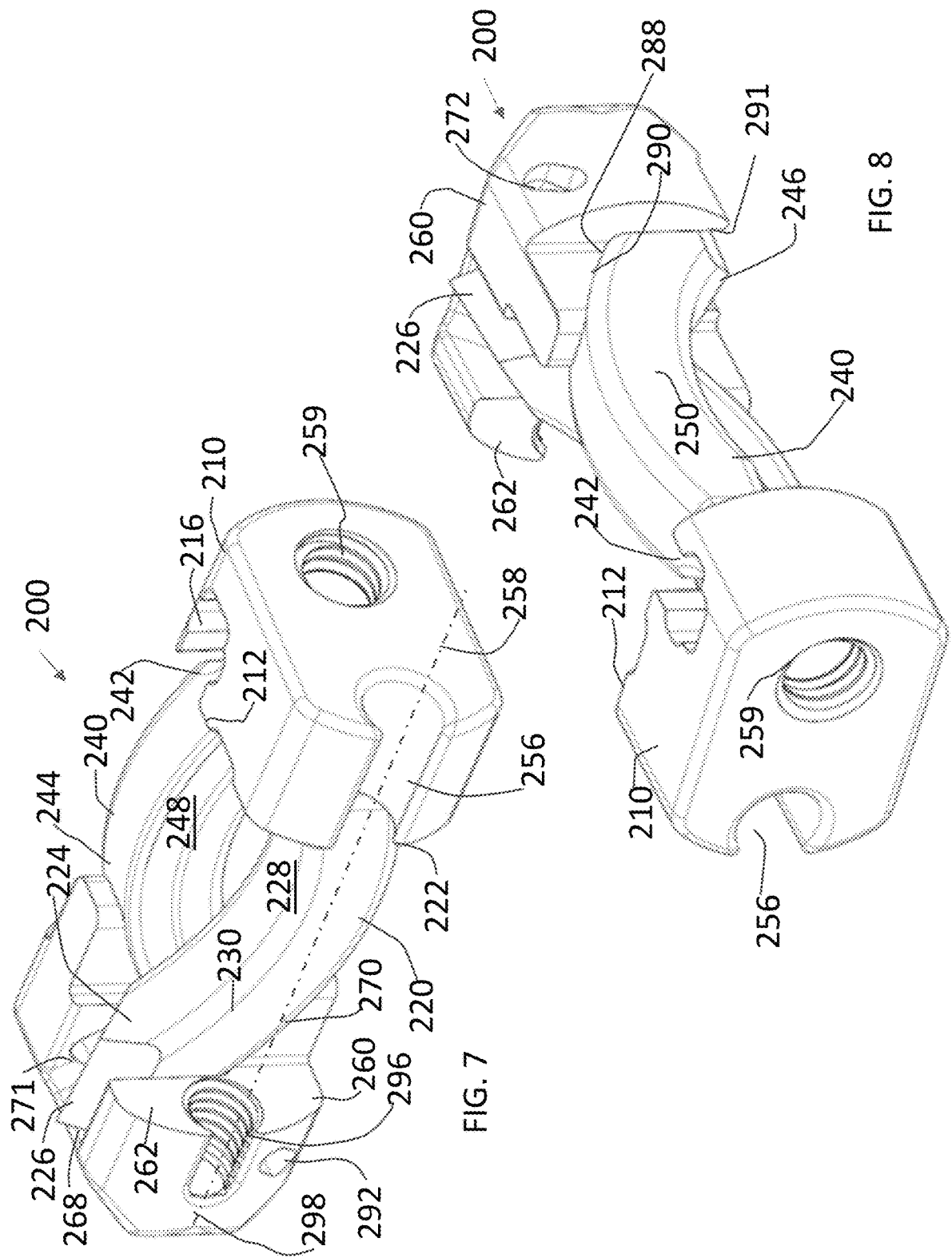

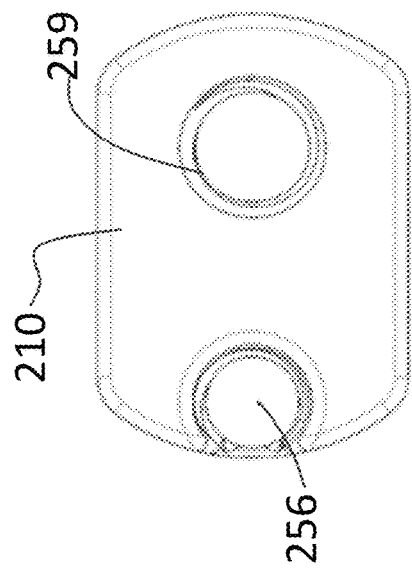
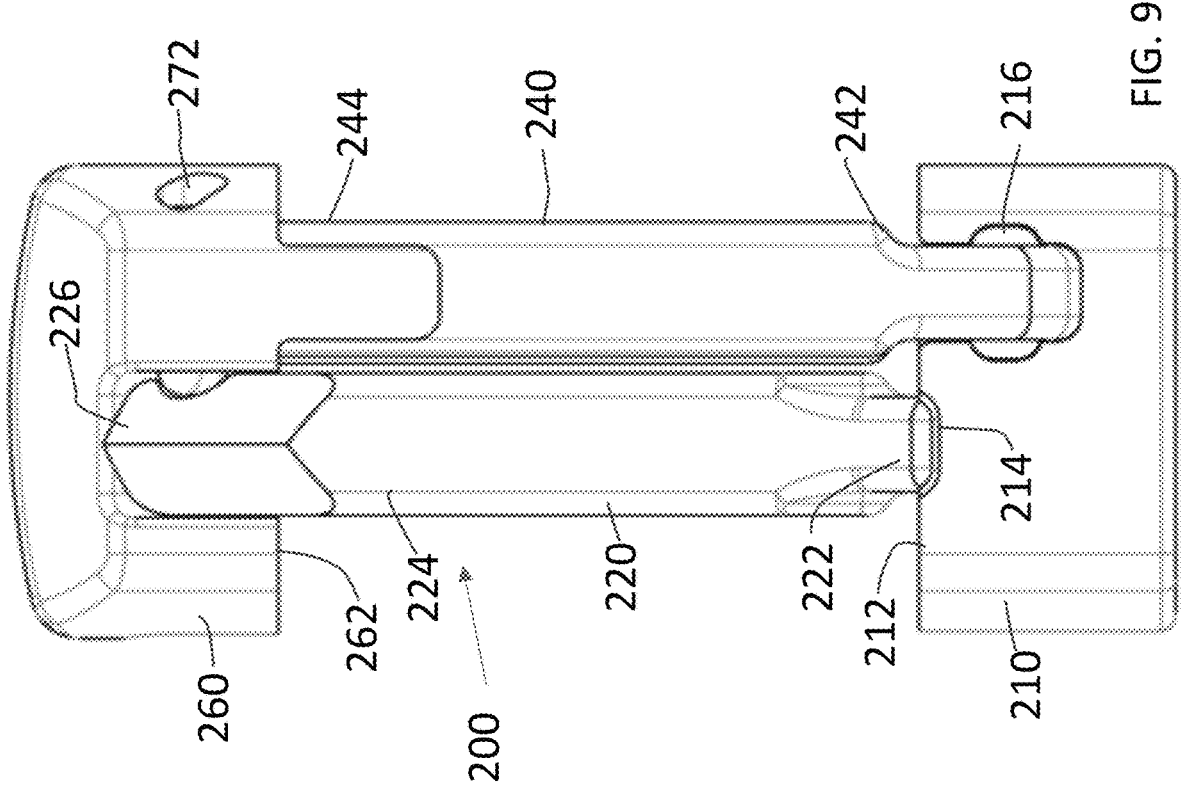

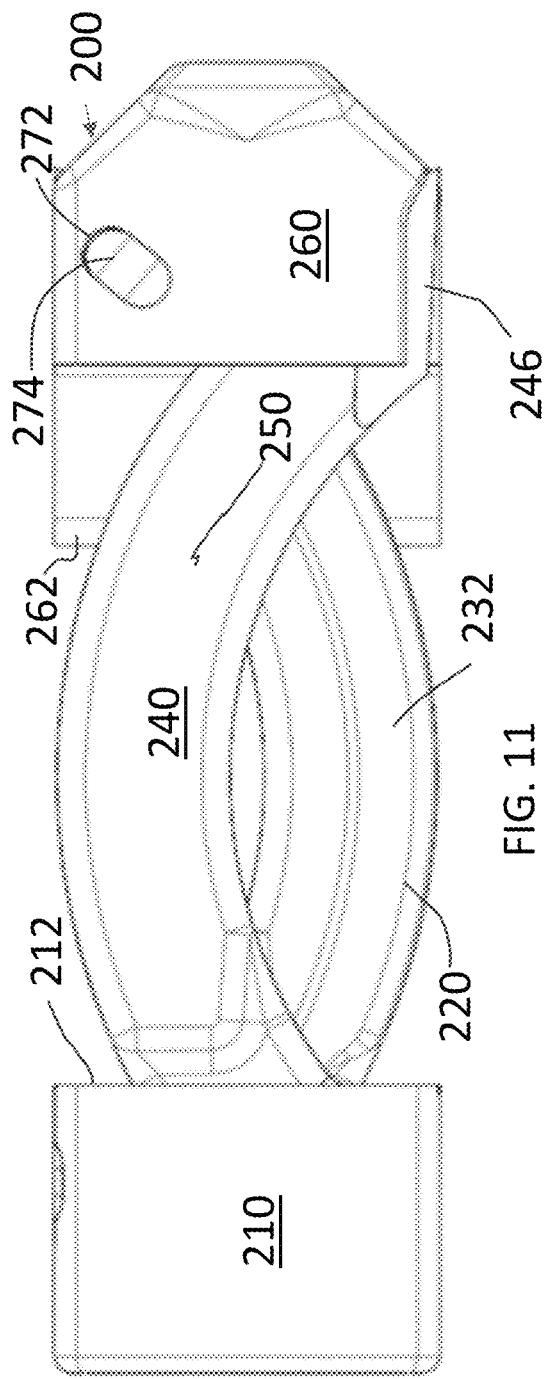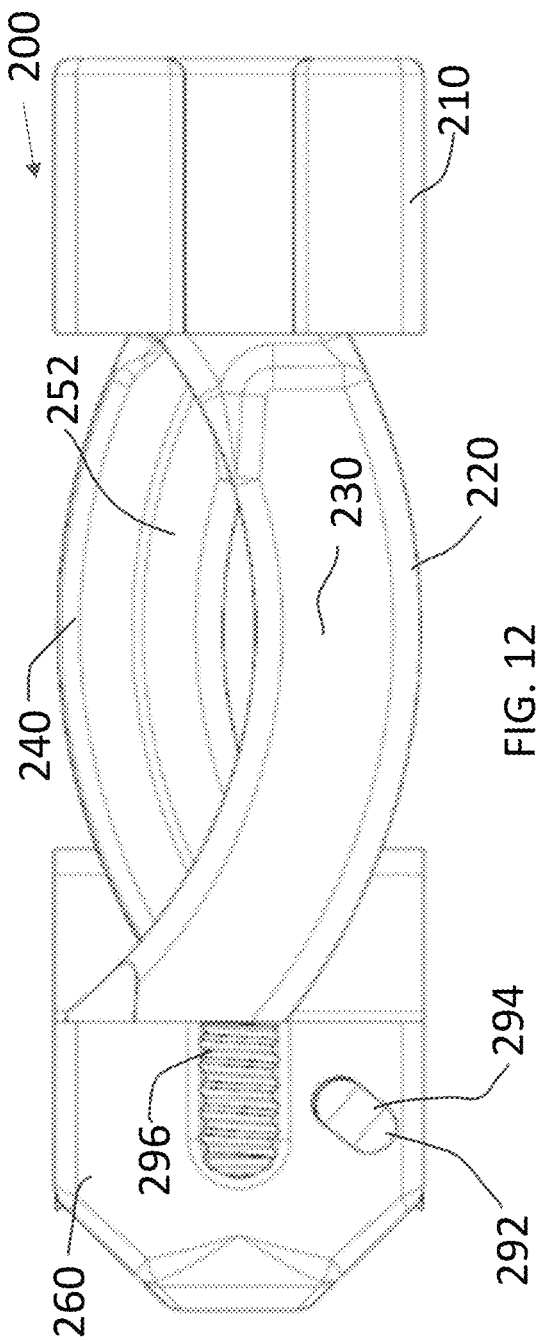

INTRADISCAL ANCHOR FIXATION DEVICE AND METHOD

BACKGROUND

Field of the Invention

The present device relates to a device and method for stabilizing two adjacent vertebral bodies as an adjunct to spinal fusion.

Description of the Related Art

Bilateral pedicle screw fixation has largely bee used to treat degenerative disc disease and a multitude of other spine pathologies as a standard of treatment to stabilize two or more adjacent vertebral bodies as an adjunct to spinal fusion. A number of iatrogenic pathologies are associated with pedicle screw fixation, including but not limited to, misplacement of screws, muscle/ligamentous disruption during insertion, adjacent segment disease due to superior adjacent facet violation by the inferior pedicle screw construct, increased procedural time, and instrumentation failure.

Accordingly, there exists a need for a fixation device and method that reduces the iatrogenic effects of a bilateral pedicle screw construct from a posterior approach while stabilizing two adjacent vertebral bodies as an adjunct to spine fusion.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to one embodiment, an intradiscal anchor fixation device may include at least one anchor configured to stabilize adjacent vertebral bodies. The device may include a plurality of anchors.

In one embodiment, the intradiscal anchor fixation device includes an anchor block and a first anchor having a pinned end pivotally connected to the anchor block and a free end, distal from the pinned end. A slide block is located distal from the anchor block and has a slide face such that the free end of the first anchor is translatable along the slide face.

In an alternative embodiment, the device includes a first block, a first anchor pivotally attached to the first block and configured to pivot in a first direction, and a second anchor pivotally attached to the first block and configured to pivot in a second direction, away from the first direction. A second block has a first slide face and a second slide face such that the first anchor is slidable along the first slide face and the second anchor is slidable along the second slide face.

In still another alternative embodiment, the device includes a first block having a first anchor pivotally attached thereto, a second anchor pivotally attached thereto, and a first through opening extending along a first axis through the first block between the first anchor and the second anchor. The device also includes a second block having a first anchor slide, a second anchor slide, and a second through opening extending along a second axis through the second block between the first anchor slide and the second anchor slide. When the first axis is aligned co-linearly with the second axis, the first anchor is slidable along the first anchor slide and the second anchor is slidable along the second anchor slide.

BRIEF DESCRIPTION OF THE DRAWINGS

Other aspects, features, and advantages of the present device will become more fully apparent from the following detailed description, the appended claims, and the accompanying drawings in which like reference numerals identify similar or identical elements.

FIG. 7 is a left perspective view of a second exemplary embodiment of an intradiscal anchor fixation device with anchors in a pre-deployed position;

FIG. 8 is a right perspective view of the intradiscal anchor fixation device of FIG. 7;

FIG. 9 is a top plan view of the intradiscal anchor fixation device of FIG. 7;

FIG. 10 is an end elevational view of the intradiscal anchor fixation device of FIG. 7;

FIG. 11 is a right side elevational view of the intradiscal anchor fixation device of FIG. 7;

FIG. 12 is a left side elevational view of the intradiscal anchor fixation device of FIG. 7;

DETAILED DESCRIPTION

Figure 1:
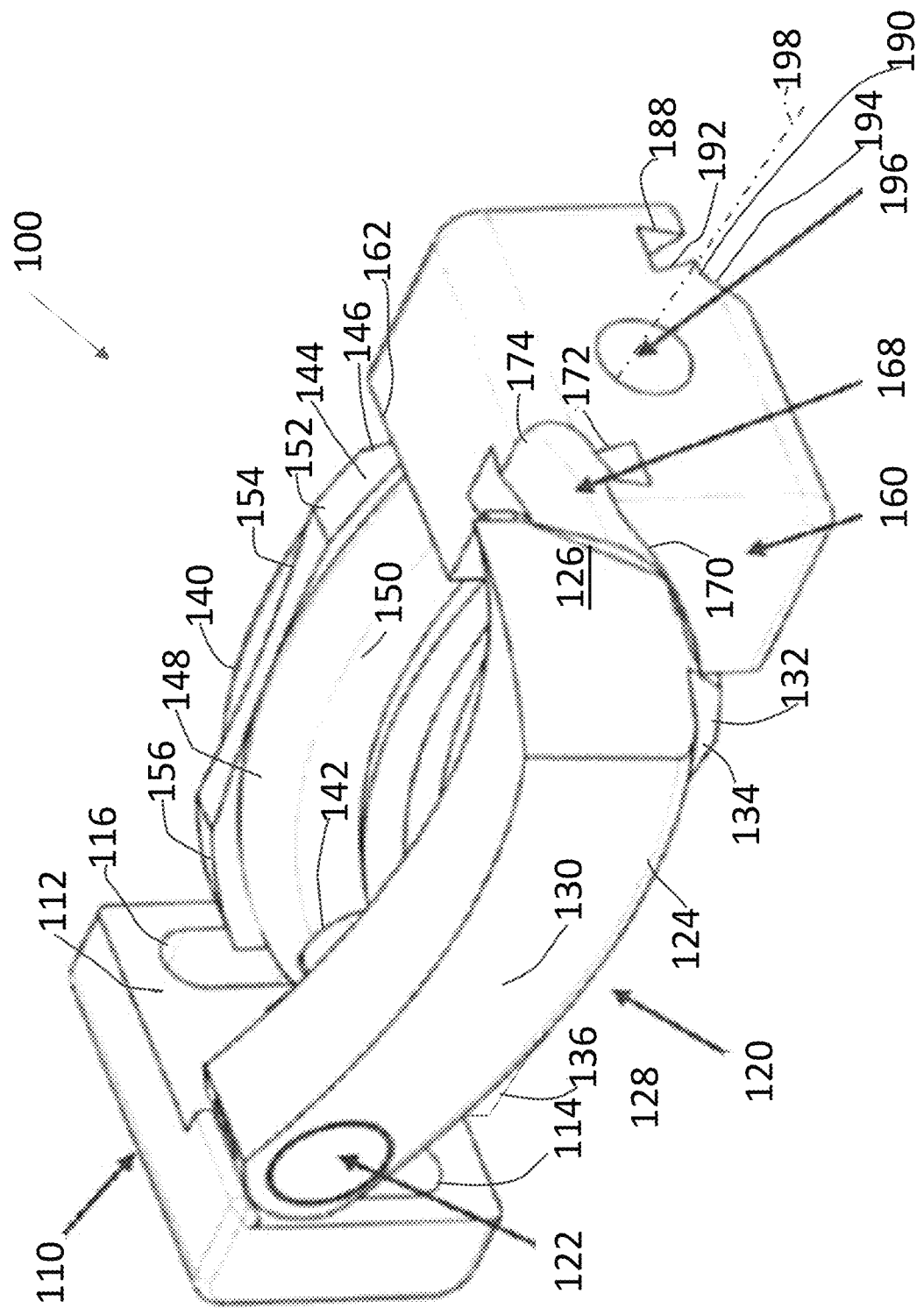
FIG. 1 is a perspective view of a first exemplary embodiment of an intradiscal anchor fixation device with anchors in a pre-deployed position.
Figure 3:
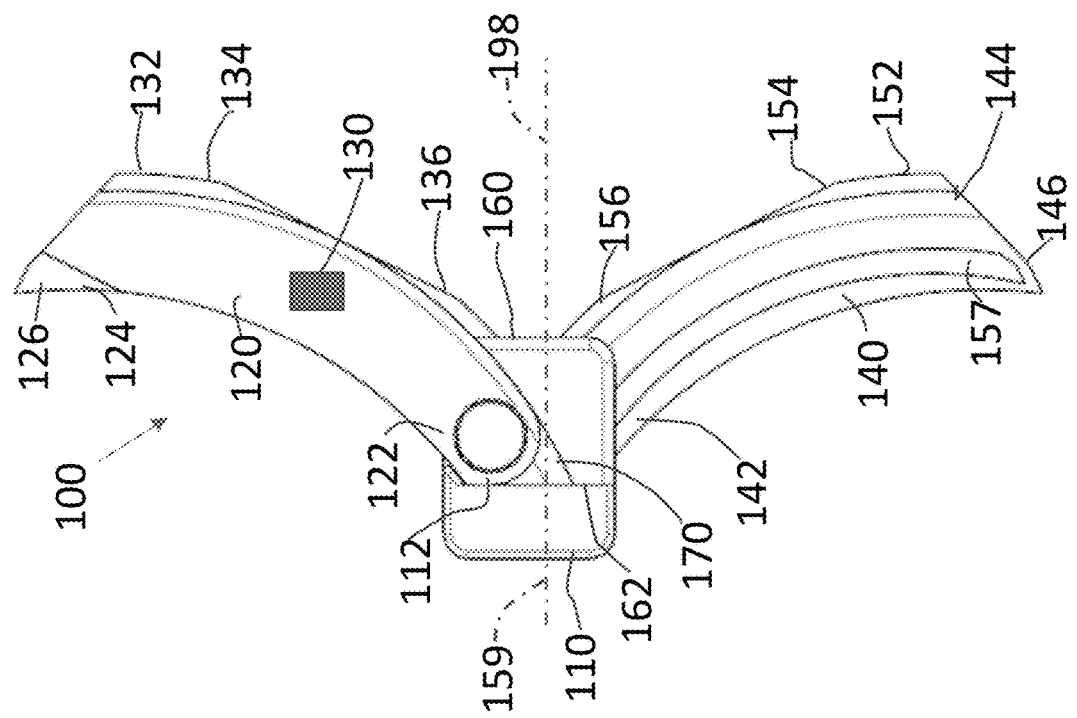
FIG. 3 is a side elevational view of the intradiscal anchor fixation device of FIG. 2.
Figure 2:
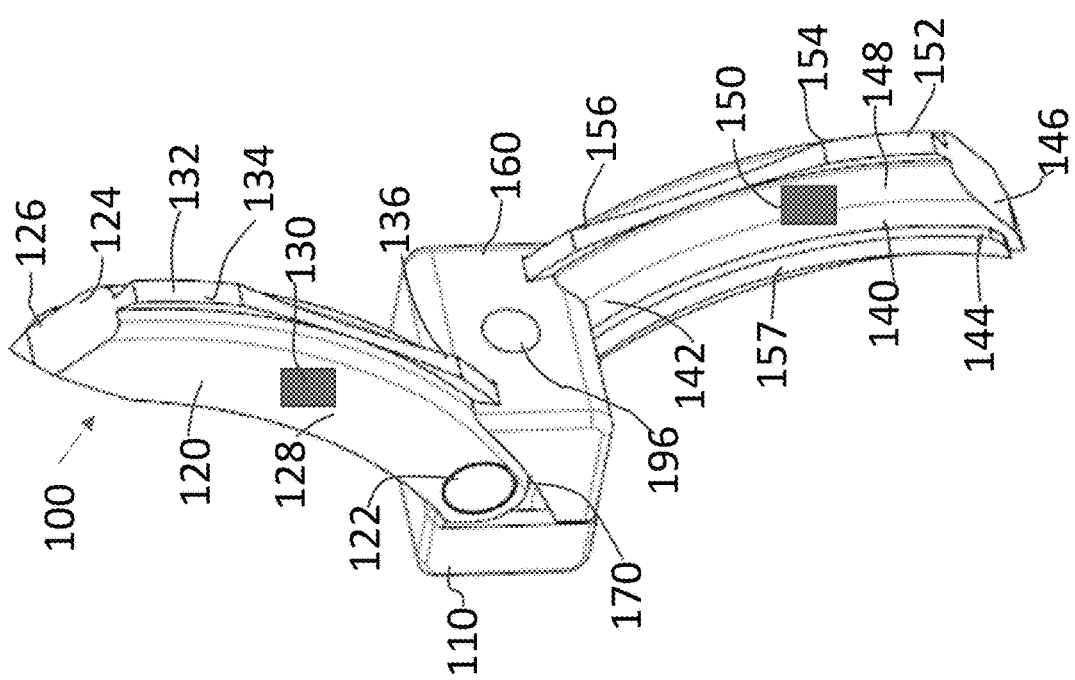
FIG. 2 is a perspective view of the intradiscal anchor fixation device of FIG. 1, with the anchors in a deployed position.
Figure 5:
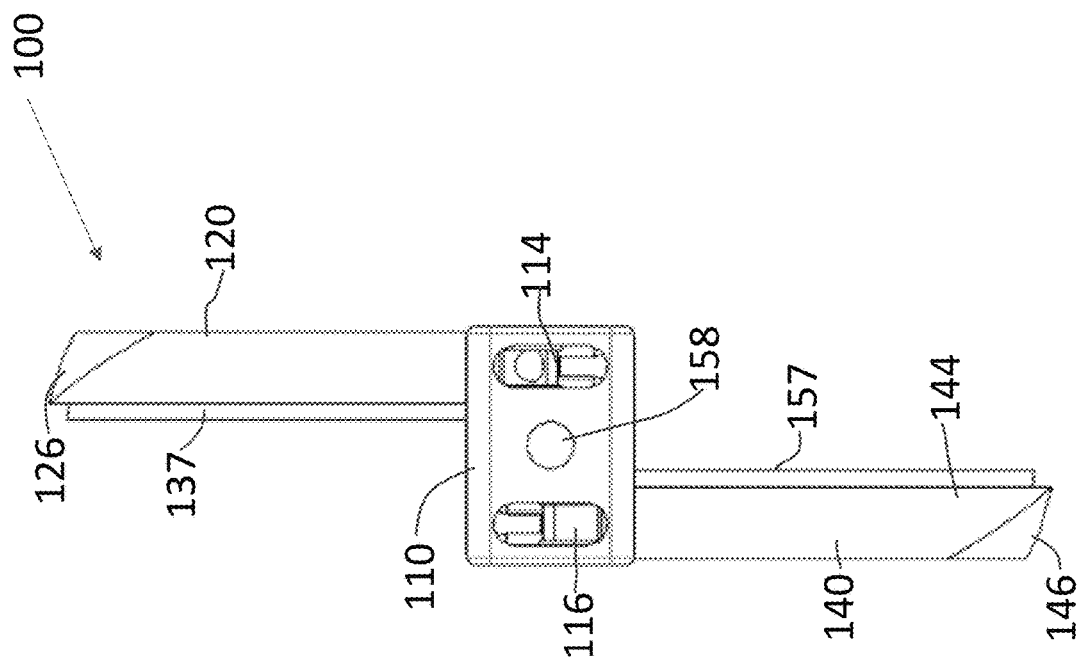
FIG. 5 is a rear side elevational view of the intradiscal anchor fixation device of FIG. 2.
Figure 4:
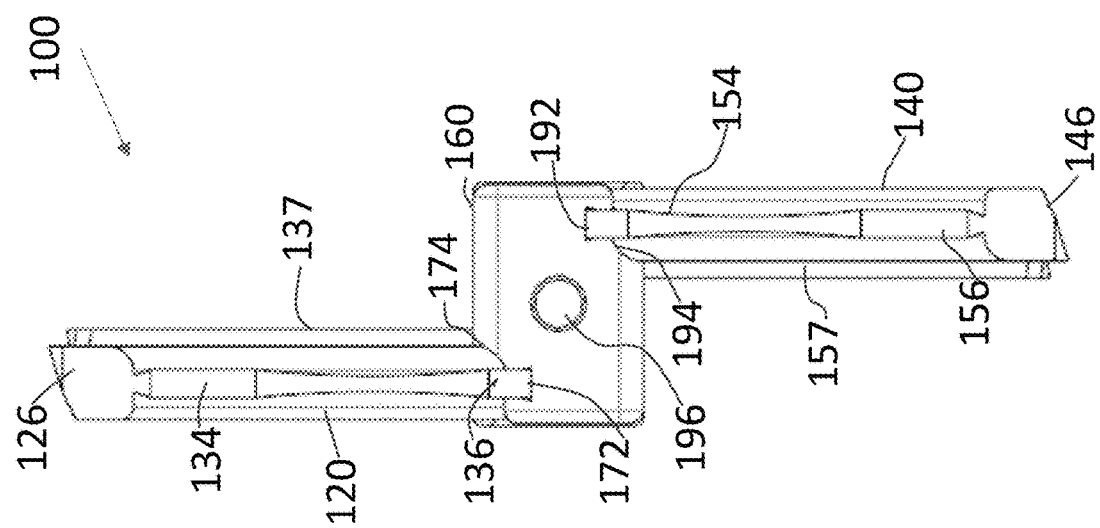
FIG. 4 is a front side elevational view of the intradiscal anchor fixation device of FIG. 2.

In the drawings, like numerals indicate like elements throughout. Certain terminology is used herein for convenience only and is not to be taken as a limitation on the present device. The terminology includes the words specifically mentioned, derivatives thereof and words of similar import. The embodiments illustrated below are not intended to be exhaustive or to limit the device to the precise form disclosed. These embodiments are chosen and described to best explain the principle of the device and its application and practical use and to enable others skilled in the art to best utilize the device.

Reference herein to "one embodiment" or "an embodiment" means that a particular feature, structure, or characteristic described in connection with the embodiment can be included in at least one embodiment of the device. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present device.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed of joining or connecting two or more elements directly or indirectly to one another, and the interposition of one or more additional elements is contemplated, although not required. Conversely, the terms "directly coupled," "directly connected," etc., imply the absence of such additional elements.

The present disclosure provides embodiments of intradiscal anchor fixation device that can be used to secure adjacent vertebrae to each other. As discussed above, iatrogenic adjacent segment disease and other surgical issues have been attributed to pedicle screw fixation. The presently disclosed device and method obviates the need for pedicle screw fixation while potentially avoiding their iatrogenic effects. Additionally, access to the disc space can be traumatic to the patient. The disclosed embodiments do not require a large access window to deploy intradiscal fixation, potentially allowing for an incision as small as 1 cm for both interbody deployment and anchor deployment. The disclosed embodiments can provide better stability in flexion, extension, or axial rotation compared with prior art fixation devices and methods used in the anterior or posterior approaches. The present method can be performed from a posterior approach, avoiding potential disruption of vasculature or nerve roots found in the anterior/lateral approaches.

Referring to FIGS. 1-5, an intradiscal anchor fixation device 100 ("fixation device 100") according to a first exemplary embodiment is shown. Fixation device 100 includes a first, or anchor, block 110 and a corresponding second, or slide, block 160 that is located distal from anchor block 110 and is adapted for translation toward anchor block 110.

Anchor block 110 includes an inward face 112 that faces slide block 160. A first anchor 120 has a first pinned end 122 pivotally connected to inward face 112 of anchor block 110 so that first anchor 120 can pivot upwardly relative to anchor block 110. First anchor 120 also includes a free end 124, distal from pinned end 122. Free end 124 includes a cutting face 126 that can cut into vertebral matter when fixation device 100 is deployed. First anchor 120 also includes an arcuate body 128 extending between pinned end 122 and free end 124. In an exemplary embodiment, first anchor body 128 can have a generally rectangular cross section.

Optionally, a piezoelectric transducer 130 can be attached to first anchor 120. Transducer 130 can be remotely operated to vibrate first anchor 120 during deployment to assist cutting face 126 in cutting into the vertebral matter.

First anchor 110 has an inferior rib 132 extending outwardly therefrom and can include a first rib section 134 spaced from a second rib section 136. In an exemplary embodiment, rib sections 134, 136 have dovetail cross sections. A first slot 114 can be cut in inward face 112 to accommodate second rib section 136 of first anchor 120 in a pre-deployment position. Optionally, first anchor 120 can also include an arcuate rib 137 that extends inwardly of first anchor 120. In an exemplary embodiment, arcuate rib 137 extends generally the length of first anchor 120.

Anchor block 110 further includes a second anchor 140, which can be identical to first anchor 120. Second anchor 140 has a pinned end 142 pivotally connected to inward face 112 of anchor block 110 so that second anchor 140 can pivot downwardly relative to anchor block 110. Second anchor 140 also includes a free end 144, distal from pinned end 142. Free end 144 includes a cutting face 146 that can cut into vertebral matter when fixation device 100 is deployed. Second anchor 140 also includes an arcuate body 148 extending between pinned end 142 and free end 144. In an exemplary embodiment, second anchor body 148 can have a generally rectangular cross section.

Optionally, a piezoelectric transducer 150 can be attached to second anchor 140. Transducer 150 can be remotely operated to vibrate second anchor 140 during deployment to assist cutting face 146 in cutting into the vertebral matter.

Second anchor 140 has a superior rib 152 extending outwardly therefrom and can include a first rib section 154 spaced from a second rib section 156. In an exemplary embodiment, rib sections 154, 156 have dovetail cross sections. A second slot 116 can be cut in inward face 112 to accommodate second rib section 156 of second anchor 140 in a pre-deployment position. Optionally, second anchor 140 can also include an arcuate rib 157 that extends inwardly of second anchor 140. In an exemplary embodiment, arcuate rib 157 extends generally the length of second anchor 140. A first through opening 158 extends along a first axis 159 through anchor block 110 between first anchor 120 and second anchor 140.

Slide block 160 includes an inward face 162 that faces anchor block 110. Slide block 160 has a first slide face 168 that has a first arcuate surface 170 extending into inward face 162. A first dovetail groove or slot 172 is formed in first arcuate surface 170 to allow first rib 132 to engage in first dovetail slot 172 in first slide face 168 so that first anchor 120 is slidable and translatable along first arcuate surface 170 of slide block 160. The engagement of rib 132 in dovetail slot 172 helps maintain alignment between anchor block 110 and slide block 160 when fixation device 100 is being deployed and also keeps first anchor 120 from being able to physically separate from slide block 160. Additionally, a side slot 174 is formed in first slide face 168 to accommodate side rib 137 as first anchor 120 slides along first slide face 168.

Similarly, slide block 160 further includes a second slide face 188 that has an arcuate surface 190 extending into inward face 162. A dovetail groove or slot 192 is formed in arcuate surface 190. Dovetail slot 192 allows rib 152 of second anchor 140 to engage in dovetail slot 192 in second slide face 188 so that second anchor 140 is slidable and translatable along arcuate surface 190 of second slide face 188. The engagement of rib 152 in dovetail slot 192 helps maintain alignment between anchor block 110 and slide block 160 when fixation device 100 is being deployed and also keeps second anchor 140 from being able to physically separate from slide block 160.

A second through opening 196 extends along a second axis 198 through the slide block 160 between first slide face 168 and second slide face 188. When first axis 159 is aligned co-linearly with second axis 198, first anchor 120 is slidable along the first anchor slide 168 and second anchor 140 is slidable along second anchor slide 188. Additionally, a side slot 194 is formed in second slide face 188 to accommodate side rib 157 as second anchor 140 slides along second slide face 188.

Figure 6:
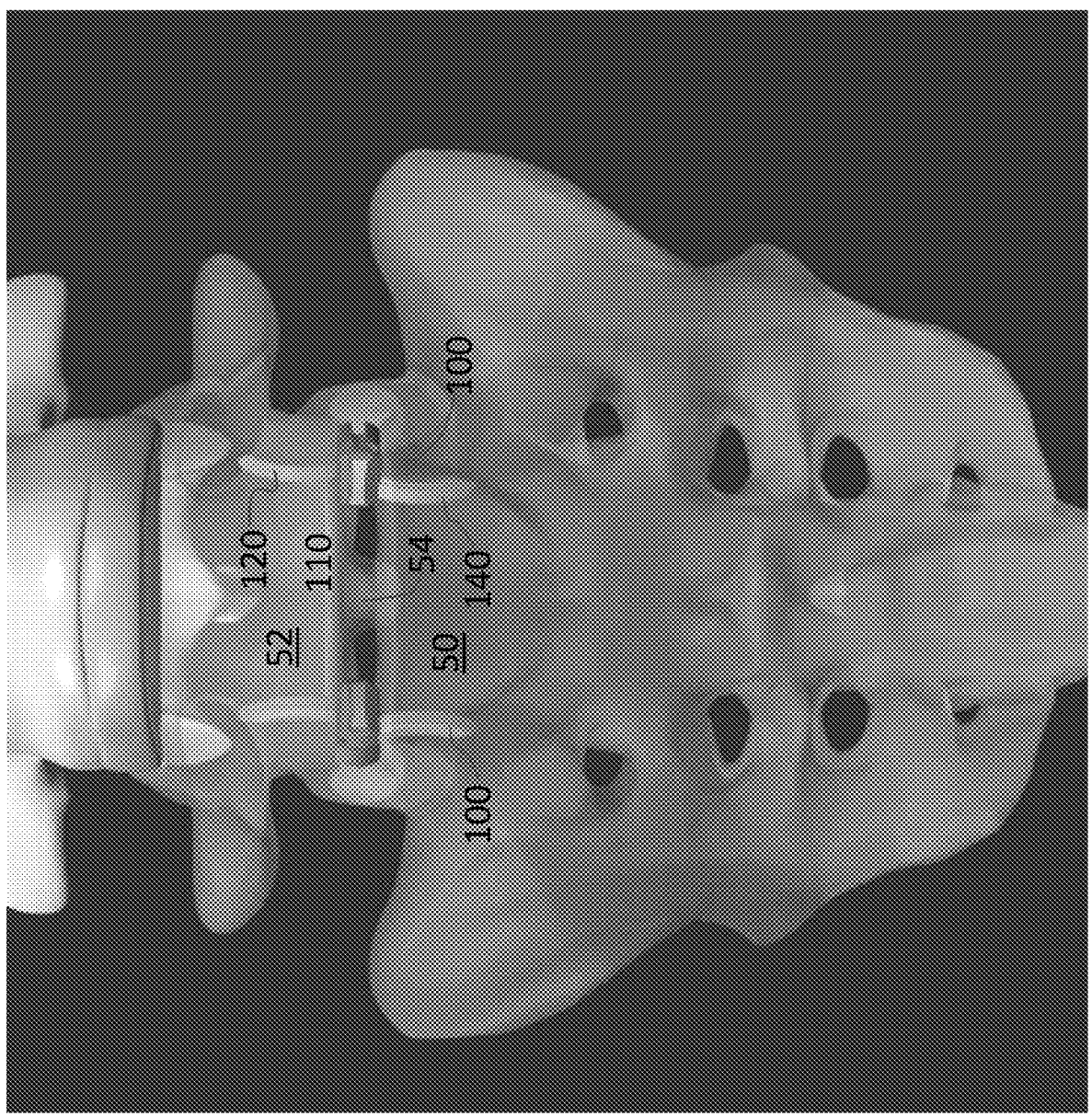
FIG. 6 is a rear elevational view of the intradiscal anchor fixation device of FIG. 2 implanted into a patient.
Figure 14:
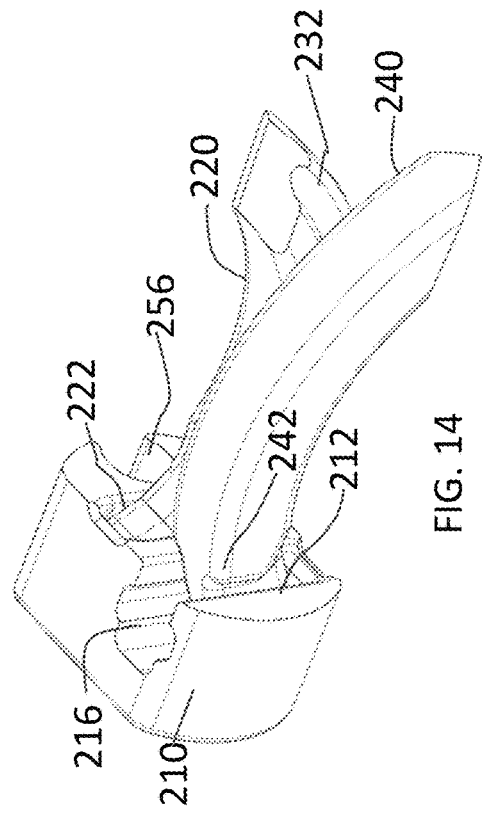
FIG. 14 is a perspective view of the anchor block and anchors used in the intradiscal anchor fixation device of FIG. 7.
Figure 15:
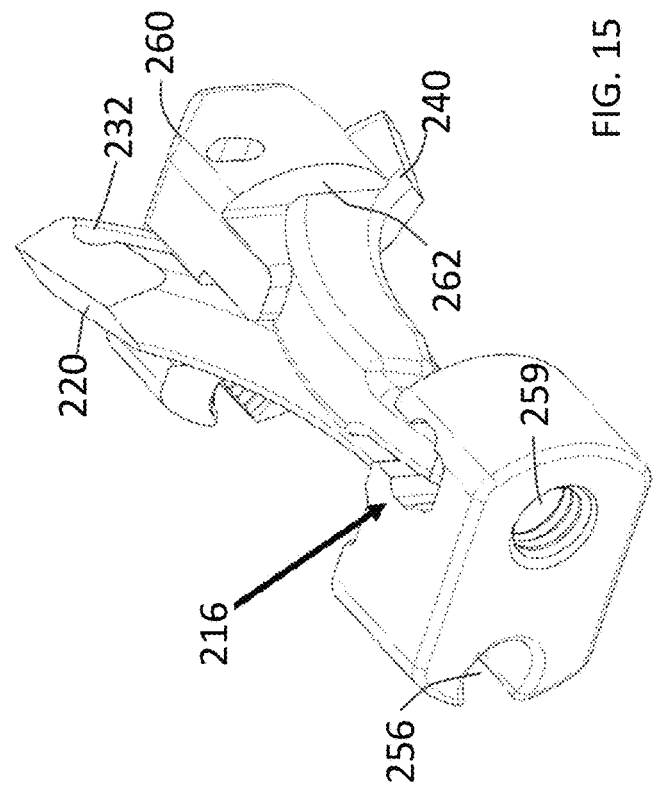
FIG. 15 is a perspective view of the intradiscal anchor fixation device of FIG. 7, with the anchors partially deployed.

One of first through opening 159 and second opening 196 can be threaded to allow for the connection of an insertion rod (not shown) so that the insertion rod can grasp fixation device 100 to insert fixation device 100 between adjacent vertebrae 50, 52. Two fixations devices 100 are shown implanted between vertebrae 50, 52 in FIG. 6.

According to one embodiment, a method of installing fixation device 100, for example, at the site of two adjacent vertebrae 50, 52, may include accessing a disc space 54 between vertebrae 50, 52 either transforaminally through Kambin's Triangle, or in a well known posterior disc access method. A tube is docked on the disc space 54 to protect the exiting and traversing nerve roots. Discectomy instrumentation is used to clear the disc space 54 for implant placement.

Placement of fixation device 100 can be navigation or robotic-guided in order to achieve clinically desirable bone purchase for optimized implant stability. Fixation device 100 can be inserted in the same orientation from which anchors 120, 140 will be deployed. Alternatively, fixation device 100 can be inserted and rotated 90 degrees depending on the geometry of blocks 110, 160 and anchors 120, 140.

When anchor block 110 is advanced toward slide block 160 so that anchors 120, 140 engage vertebrae 50, 52, respectively, first anchor 120 translates in a downward curvilinear direction along a first plane and second anchor 140 translates in an upward curvilinear direction along a second plane such that the first plane is parallel to the second plane.

An implant (not shown) can be inserted in the same direction from which anchors 120, 140 are deployed. Alternatively, the implant can be inserted and rotated 90 degrees depending on the geometry of blocks 110, 160 and anchors 120, 140. Optionally, the implant can be inserted with a curve trajectory facing anteriorly or posteriorly.

An alternative embodiment of an intradiscal anchor fixation device 200 ("fixation device 200") is shown in FIGS. 7-17. Fixation device 200 includes a first, or anchor, block 210 and a corresponding second, or slide, block 260 that is located distal from anchor block 210 and is adapted for translation toward anchor block 210.

Figure 13:
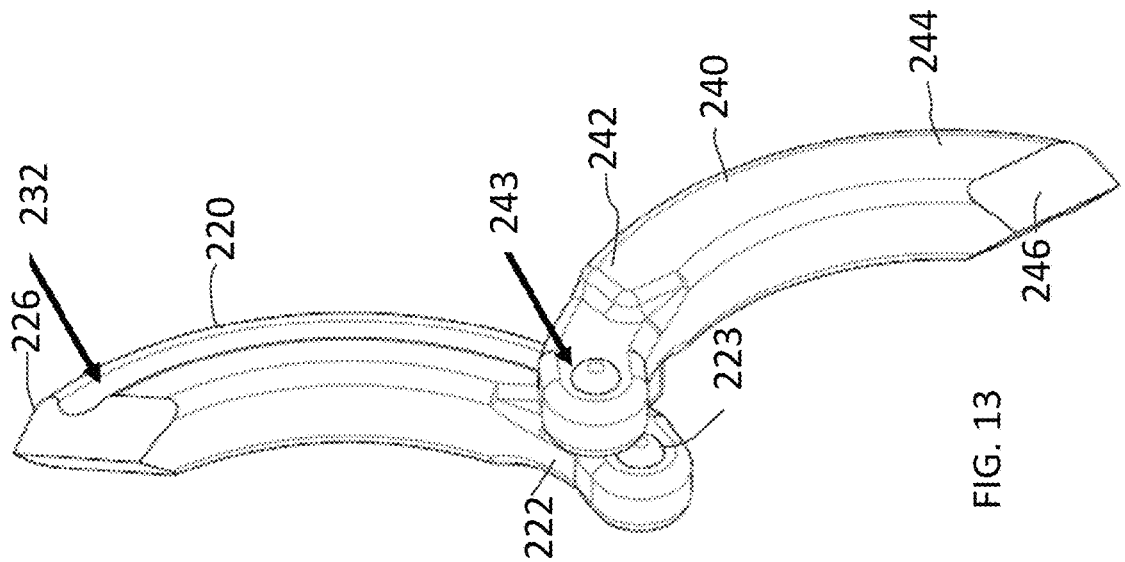
FIG. 13 is a perspective view of the anchors used in the intradiscal anchor fixation device of FIG. 7.

Anchor block 210 includes an inward face 212 that faces slide block 260. A first anchor 220 has a first pinned end 222 pivotally connected to inward face 212 of anchor block 210 so that first anchor 220 can pivot upwardly relative to anchor block 210. Anchor block 210 includes a first cavity 214 that extends inferiorly and allows for the connection of pinned end 222 and also allows for the pivoting of first anchor 220 in a superior direction. Referring to FIG. 13, pinned end 222 includes an anchor retaining feature 223 that slides into first cavity 214 and allows for the pivoting of first anchor 220 without locking first anchor 220 into anchor block 210. In an exemplary embodiment, anchor retaining feature 223 can be an arcuate surface to facilitate the pivoting rotation of first anchor 220 with respect to anchor block 210.

First anchor 220 also includes a free end 224, distal from pinned end 222. Free end 224 includes a cutting face 226 that can cut into vertebral matter when fixation device 200 is deployed. First anchor 220 also includes an arcuate body 228 extending between pinned end 222 and free end 224. In an exemplary embodiment, first anchor body 228 can have a generally rectangular cross section.

Optionally, a piezoelectric transducer 230 can be attached to first anchor 220. Transducer 230 can be remotely operated to vibrate first anchor 220 during deployment to assist cutting face 226 in cutting into the vertebral matter.

First anchor 210 has an arcuate pin groove 232 that extends inwardly of first anchor 220. In an exemplary embodiment, arcuate pin groove 232 extends generally the length of first anchor 220.

Anchor block 210 further includes a second anchor 240, which can be identical to first anchor 220. Second anchor 240 has a pinned end 242 pivotally connected to inward face 212 of anchor block 210 so that second anchor 240 can pivot downwardly relative to anchor block 210. Anchor block 210 also includes a second cavity 216 that extends superiorly and allows for the connection of pinned end 242 and also allows for the pivoting of second anchor 240 in an inferior direction. Referring to FIG. 13, pinned end 242 includes an anchor retaining feature 243 that slides into second cavity 216 and allows for the pivoting of second anchor 240 without locking second anchor 240 into anchor block 210. In an exemplary embodiment, anchor retaining feature 243 can be an arcuate surface to facilitate the pivoting rotation of second anchor 240 with respect to anchor block 210.

Second anchor 240 also includes a free end 244, distal from pinned end 242. Free end 244 includes a cutting face 246 that can cut into vertebral matter when fixation device 200 is deployed. Second anchor 240 also includes an arcuate body 248 extending between pinned end 242 and free end 244. In an exemplary embodiment, second anchor body 248 can have a generally rectangular cross section.

Optionally, a piezoelectric transducer 250 can be attached to second anchor 240. Transducer 250 can be remotely operated to vibrate second anchor 240 during deployment to assist cutting face 246 in cutting into the vertebral matter.

Second anchor 240 has an arcuate pin groove 252 that extends inwardly of first anchor 240. In an exemplary embodiment, arcuate pin groove 252 extends generally the length of first anchor 240.

A first through opening 256 extends along a first axis 258 through anchor block 210 adjacent to first anchor 220 and distal from second anchor 240. First through opening 256 is unthreaded. A threaded opening 259 is formed in a rear face 213 of anchor block 210, distal from inward face 212. Threaded opening 259 provides a connection access for an insertion tool (not shown).

Slide block 260 includes an inward face 262 that faces anchor block 210. Slide block 260 has a first slide face 268 that has a first arcuate surface 270 extending into inward face 262 and having a superior opening 271 to allow free end 224 of anchor 220 to slide along first arcuate surface 270 and extend superiorly of slide block 260.

Figure 17:
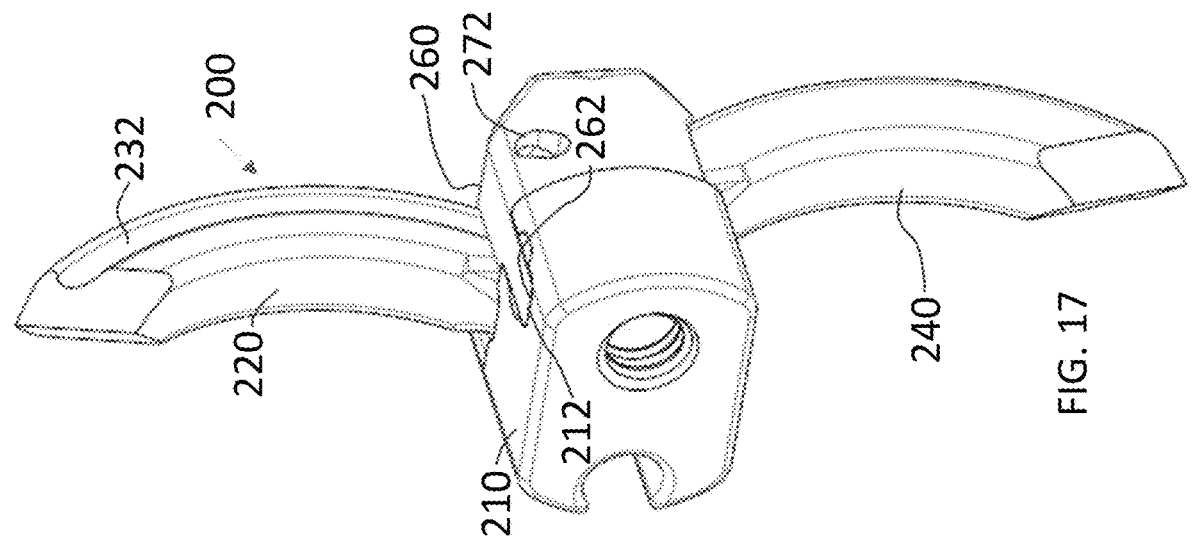
FIG. 17 is a right perspective view of the intradiscal anchor fixation device of FIG. 16.
Figure 16:
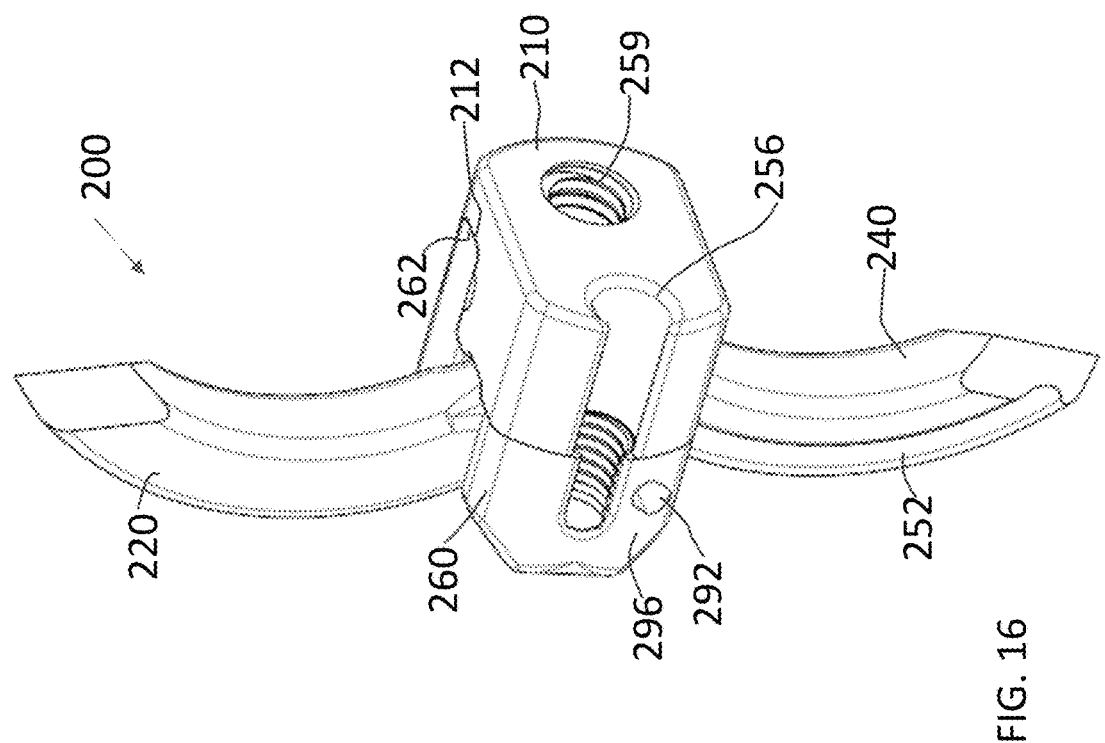
FIG. 16 is a left perspective view of the intradiscal anchor fixation device with anchors in a deployed position.

Inward face 262 of slide block 260 is complementary to inward face 212 of anchor block 210 such that, when slide block 260 s advanced toward anchor block 210 to fully extend anchors 220, 240, as shown in FIGS. 16 and 17, inward faces 212, 262 engage and mate with each other. Referring to FIG. 11, a first retaining pin slot 272 extends transversely through slide block 260 from a superior position and communicates with first slide face 268. A retaining pin 274 is inserted into retaining pin slot 272 and extends into first slide face 268 to engage with arcuate pin groove 232 so that first anchor 220 is slidable and translatable along first arcuate surface 270 of slide block 260. The engagement of arcuate pin groove 232 with retaining pin 274 helps maintain alignment between anchor block 210 and slide block 260 when fixation device 200 is being deployed and also keeps first anchor 220 from being able to physically separate from slide block 260.

Similarly, slide block 260 further includes a second slide face 288 that has an arcuate surface 290 extending into inward face 262 and having an inferior opening 291 to allow free end 244 of anchor 240 to slide along second arcuate surface 290 and extend inferiorly of slide block 260. Referring to FIG. 12, a second retaining pin slot 292 extends transversely through slide block 260 from an inferior position and communicates with second slide face 288. A retaining pin 294 is inserted into retaining pin slot 292 and extends into second slide face 288 to engage with arcuate pin groove 252 so that second anchor 240 is slidable and translatable along second arcuate surface 290 of slide block 260. The engagement of arcuate pin groove 252 with retaining pin 294 helps maintain alignment between anchor block 210 and slide block 260 when fixation device 200 is being deployed and also keeps second anchor 240 from being able to physically separate from slide block 260.

Referring to FIG. 7, a second threaded opening 296 extends along a second axis 298 through the slide block 260 above second retaining pin slot 292 and adjacent first slide face 268, distal from second slide face 288. When first axis 258 is aligned co-linearly with second axis 298, first anchor 220 is slidable along the first anchor slide 268 and second anchor 240 is slidable along second anchor slide 288. Additionally, a fixation device can be inserted into first through opening 256 and into second threaded opening 296.

According to one embodiment, a method of installing fixation device 200, for example, at the site of two adjacent vertebrae 50, 52, may include accessing a disc space 54 between vertebrae 50, 52 either transforaminally through Kambin's Triangle, or in a well known posterior disc access method. A tube is docked on the disc space 54 to protect the exiting and traversing nerve roots. Discectomy instrumentation is used to clear the disc space 54 for implant placement.

Placement of fixation device 200 can be navigation or robotic-guided in order to achieve clinically desirable bone purchase for optimized implant stability. Fixation device 200 can be inserted in the same orientation from which anchors 220, 240 will be deployed. Alternatively, fixation device 100 can be inserted and rotated 90 degrees depending on the geometry of blocks 110, 160 and anchors 120, 140.

When anchor block 210 is advanced toward slide block 260 so that anchors 220, 240 engage vertebrae 50, 52, respectively, first anchor 220 translates in an upward curvilinear direction along a first plane and second anchor 240 translates in a downward curvilinear direction along a second plane, as shown in FIGS. 16 and 17, such that the first plane is parallel to the second plane.

An implant (not shown) can be inserted in the same direction from which anchors 220, 240 are deployed. Alternatively, the implant can be inserted and rotated 90 degrees depending on the geometry of blocks 210, 260 and anchors 220, 240. Optionally, the implant can be inserted with a curve trajectory facing anteriorly or posteriorly.

Once fixation device 200 is fully inserted, fixation device 200 can be locked in place by inserting a rod (not shown) through first through opening 256 and threading the rod into second threaded opening 296.

While fixation device 100 provides for both anchors 120, 140 to be pivotally connected to anchor base 110 and, similarly, fixation device 200 provides for both anchors 220, 240 to be pivotally connected to anchor base 210, those skilled in the art will recognize that one of anchor 120, 140 and anchor 220, 240 can alternatively be pivotally connected to a respective slide block 160, 260.

It will be further understood that various changes in the details, materials, and arrangements of the parts which have been described and illustrated in order to explain the nature of this device may be made by those skilled in the art without departing from the scope of the device as expressed in the following claims.

What is claimed is:
1. An intradiscal anchor fixation device comprising:
an anchor block having a first opening extending along a first axis and a second opening extending along a second axis;
a first anchor having a pinned end pivotally connected to the anchor block and a free end, distal from the pinned end; and
a slide block having a first opening extending along the first axis and distal from the anchor block and having a slide face such that the free end of the first anchor is translatable along the slide face,
wherein the slide block is adapted for translation toward the anchor block from a first position to a second position,
wherein, when the slide block is in the second position, the free end of the first anchor extends distally beyond the slide block,
wherein the slide block includes a retaining slot configured to receive a retaining pin,
wherein the retaining pin is configured to engage with the first anchor, and wherein the first opening on the anchor block is unthreaded and the second opening on the anchor block is threaded.

2. The intradiscal anchor fixation device according to claim 1, wherein the first anchor comprises an arcuate body.

3. The intradiscal anchor fixation device according to claim 2, wherein the first anchor comprises a rectangular cross section.

4. The intradiscal anchor fixation device according to claim 1, wherein the free end comprises a cutting face.

5. The intradiscal anchor fixation device according to claim 1, further comprising a piezoelectric transducer attached to the first anchor.

6. The intradiscal anchor fixation device according to claim 1, wherein the slide face comprises a groove formed therein.

7. The intradiscal anchor fixation device according to claim 6, wherein the first anchor comprises a rib extending outwardly therefrom, wherein the rib is configured to slide along the groove.

8. The intradiscal anchor fixation device according to claim 1, wherein the device further comprises a second anchor pivotally connected to the anchor block.

\* \* \* \* \*